US00PP20268P2

(12) United States Plant Patent
Jones

(10) Patent No.: US PP20,268 P2
(45) Date of Patent: Sep. 8, 2009

(54) ***NEMESIA* PLANT NAMED 'PENDROP'**

(50) Latin Name: *Nemesia×hybrida*
Varietal Denomination: PENDROP

(76) Inventor: Sidney Jones, Netherwent Magor, Newport, Gwent (GB), NPG SAU ( * ) Notice: Subject to any disclaimer, the term of this patent is extended or adjusted under 35 U.S.C. 154(b) by 24 days.

(21) Appl. No.: 12/004,955

(22) Filed: Dec. 26, 2007

Related U.S. Application Data

(60) Provisional application No. 60/920,580, filed on Mar. 28, 2007.

(51) Int. Cl.
*A01H 5/00* (2006.01)

(52) U.S. Cl. ..... Plt./458

(58) Field of Classification Search ..... Plt./458
See application file for complete search history.

(56) References Cited

PUBLICATIONS

UPOV–ROM GTITM Plant Variety Database, Mar. 2008, GTI Jouve Retrieval Software, Citation for Nemesia 'Pendrop', one page.*

* cited by examiner

*Primary Examiner*—June Hwu

(57) ABSTRACT

A new and distinct cultivar of *Nemesia* plant named 'Pendrop' that is characterized by a compact habit, pale green foliage, short stems, and purple and white flowers with a prominent yellow palate. In combination, these characteristics set 'Pendrop' apart from all other existing varieties of *Nemesia* known to the inventor.

2 Drawing Sheets

Genus: *Nemesia.*
Species: ×*hybrida.*
Denomination: 'Pendrop'.

BACKGROUND OF THE INVENTION

The present invention relates to a new and distinct cultivar of *Nemesia* plant that is grown as an ornamental plant for use in a border, patio container or hanging basket. The new cultivar is known botanically as *Nemesia×hybrida* and will be referred to hereinafter by the cultivar name 'Pendrop'.

The new *Nemesia* variety named 'Pendrop' is the product of a breeding program established by the inventor in 2001 at the inventor's nursery in Netherwent, Wales, United Kingdom. The purpose of the breeding program is to produce new compact sterile *Nemesia* varieties with a high ratio of flower to leaf.

'Pendrop' is a seedling selection arising from the inventor's crossing of own parent lines which were never released as commercial varieties or patented. 'Pendrop' was selected in 2002 for its floriferousness, sterile flowers, very compact habit and attractive bi-colored flowers.

In order to achieve the desired combination of sterility and compactness of a new variety of *Nemesia,* the inventor chose parents (from his previously-raised seedlings) which were barely fertile and also naturally compact. Both of the parents of 'Pendrop' possessed a short growth habit. One parent bore entirely pink flowers. The other parent bore flowers which were bi-colored pink and yellow and also exhibited larger leaves than 'Pendrop'. Neither parent exhibited the characteristic prominent yellow palate of 'Pendrop'.

The closest commercial variety known to the inventor is the inventor's variety *Nemesia* 'Pengoon' (U.S. Plant Pat. No. 14,261). In comparison to 'Pengoon', 'Pendrop' is more compact and has bi-colored flowers; the flowers of 'Pengoon' are uniformly blue in color.

'Pendrop' was first asexually propagated by the inventor at the inventor's nursery in Netherwent, Wales, United Kingdom in 2003 using tip cuttings. 'Pendrop' has subsequently be asexually propagated, using tip and branch cuttings, and has been determined to reproduce true to type in successive generations of asexual reproduction.

An application for European Plant Breeder Rights was filed on Oct. 25, 2005, with application number 2005/2041. The first sales or public distribution of 'Pendrop' occurred on Apr. 1, 2006, at the inventor's nursery in Wales, United Kingdom.

SUMMARY OF THE INVENTION

The following traits have been repeatedly observed and represent the distinguishing characteristics of 'Pendrop'. In combination these traits set the new cultivar apart from all other existing varieties of *Nemesia* known to the inventor. 'Pendrop' has not been tested under all possible conditions and phenotypic differences may be observed with variations in environmental, climatic, and cultural conditions, however, without any variance in genotype.

1. 'Pendrop' bears pale green foliage.
2. 'Pendrop' bears purple and white flowers with a prominent yellow palate.
3. 'Pendrop' has short stems.
4. 'Pendrop' is compact in habit.
5. 'Pendrop' is suitable for use as a garden or landscape plant.
6. 'Pendrop' is hardy to USDA Zone 6.

BRIEF DESCRIPTION OF THE DRAWINGS

The accompanying drawings illustrate the distinguishing traits and overall appearance of the new *Nemesia* cultivar 'Pendrop'. The plant photographed is one year old, and has been grown in an unheated greenhouse in Netherwent, Wales, United Kingdom.

The drawing labeled as FIG. 1 illustrates the entire plant.

Figure 1:
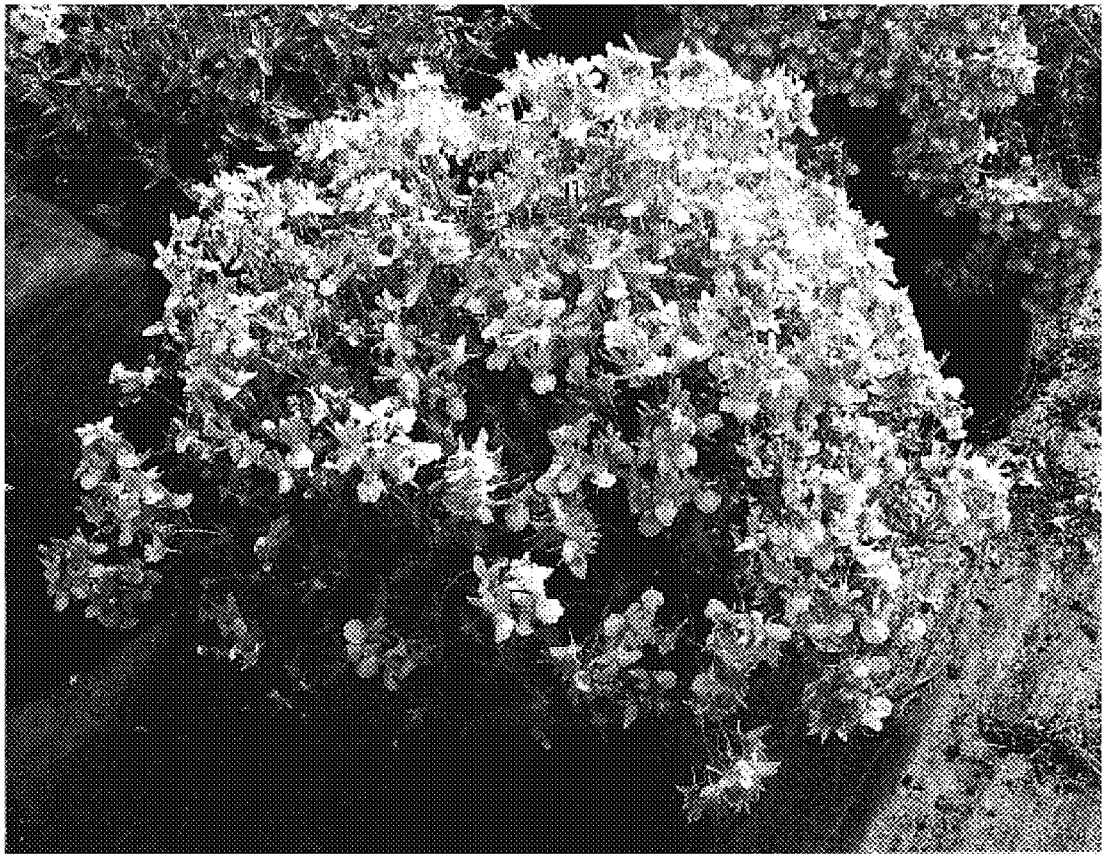
Figure 2:
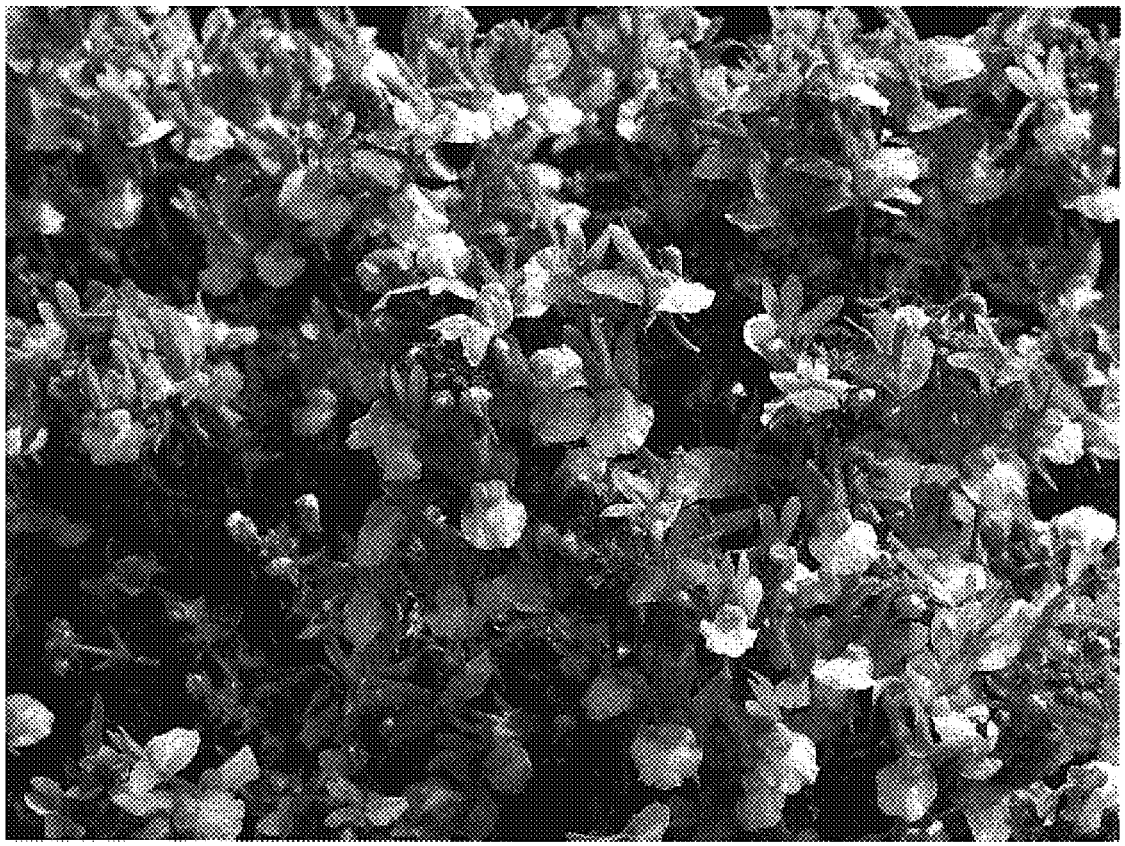

The drawing labeled as FIG. 2 presents a close-up of the flowers.

The drawings were made using conventional photographic techniques and the laser copies were made using standard techniques. Although colors may appear different from actual colors due to light reflectance, they are as accurate as possible by conventional photography and laser copying.

BOTANICAL DESCRIPTION OF THE PLANT

The following is a detailed description of the *Nemesia* plant named 'Pendrop'. Data was collected in Cambridgeshire, United Kingdom from plants grown in 9 cm containers under greenhouse conditions. Phenotypic differences may be observed with variations in environmental, climatic, and cultural conditions. The color determinations are in accordance with The Royal Horticultural Society Colour Chart except where general color terms of ordinary dictionary significance are used. The growing requirements are similar to other *Nemesia* plants.

Botanical classification: *Nemesia×hybrida* 'Pendrop'.
Common name: *Nemesia.*
Use: Bedding and patio plant.
Parentage: Unnamed parents from inventor's breeding program.
Propagation: Tip cuttings.
Sexuality: Hermaphrodite.
Vigor: Average.
Growth habit: Rounded, freely branching.
Plant dimensions: 17 cm in height and 17 cm in width.
Type: Annual or Perennial in USDA Zones 6 and higher.
Time to initiate roots: Approximately 14 days at temperatures of 18° Centigrade is required to produce rooted cuttings.
Crop time: 21 days are required to reach commercial size from a rooted cutting.
Culture requirements: Moderately fertile soil in semi-shade to full sun.
Uses: Pots, patio containers, planting in open border.
Pest and disease resistance or susceptibility: In common with *Nemesias* and annual bedding plants generally, Pendrop is susceptible to pests including aphids and red spider mites; and diseases including *botrytis* which may result from poor air circulation. Pendrop has not been observed to exhibit any particular resistance or susceptibility to pests and diseases.
Root system: Numerous and fine.
Hardiness: Hardy to USDA Zone 6.
Branching habit: Very free.
Stem:
- *Dimensions, main stem.*—Overall length 17 cm; cross-section 1.5 mm.
- *Lateral shoot, angle at emergence.*—Angle acute — approximately 30°.
- *Color.*—144A.
- *Shape of cross-section.*—Square.
- *Surface pubescence.*—None.
- *Lenticels.*—Absent.
- *Length of internode.*—25 mm.
- *Leaf arrangement.*—Opposite.
- *Leaf attachment.*—Sessile.
- *Petioles.*—Absent.
- *Stipules.*—Absent.

Leaf:
- *Shape.*—Ovate-Elliptic.
- *Dimensions.*—30 mm in length and 10 mm in width.
- *Margin.*—Sparsely serrate.
- *Division.*—Absent; leaf entire.
- *Apex.*—Acute.
- *Base.*—Acuminate.
- *Color, adaxial surface.*—137A.
- *Color, abaxial surface.*—137C.
- *Texture.*—Glabrous.
- *Venation pattern.*—Pinnate.
- *Venation color, adaxial surface.*—143C at base, becoming 137A towards apex.
- *Venation color, abaxial surface.*—143C.
- *Fragrance.*—Absent.

Flowers:
- *Arrangement.*—Simple raceme, with further racemes emerging from axils of the upper leaves.
- *Inflorescence, number of flowers.*—25, opening sequentially.
- *Inflorescence, spacing of flowers.*—Congested: flower spacing very uneven, occasionally 15–20 mm, often nearly opposite or so close as to appear to be in whorls of 3 or more.
- *Blooming season.*—March to September; year-round in southern regions of the U.S.
- *Lastingness of the flowers.*—Approximately 1 week in cool climates with cool nights, reducing to 2–3 days in hot climates with warm nights.
- *Peduncle.*—Dimensions: 40 mm in length below first flower, 1 mm in diameter.
- *Peduncle cross-section.*—Square.
- *Peduncle color.*—144A.
- *Peduncle pubescence.*—Sparsely furnished with minute glandular hairs.
- *Pedicel dimensions.*—12 mm in length and approximately 0.5 mm in diameter.
- *Pedicel color.*—144A.
- *Pedicel pubescence.*—Moderately clothed with minute glandular hairs too fine to color match.
- *Bud shape.*—In lateral section broader than high, the lower part more bulbous than the upper.
- *Bud dimensions.*—13 mm in length and 6 mm in width.
- *Bud color.*—56A.
- *Flowers, persistent or self-cleaning.*—Self-cleaning.
- *Flower type, single or double.*—Single.
- *Flower fragrance.*—Strong, vanilla-like.
- *Flower shape.*—See corolla below.
- *Flower aspect.*—Facing slightly upward.
- *Calyx.*—Overall dimensions: 2 mm in length and 6 mm in diameter. Pubescence: Moderately clothed with minute glandular hairs too fine to color match. Color: 138A. Number of sepals: Five.
- *Sepals.*—Dimensions: 3 mm in length and 1 mm in width. Shape: Ovate-elliptic. Apex: Acute. Margin: Entire.
- *Corolla.*—Shape: Zygomorphic. Overall dimensions: 20 mm in height and 14 mm in width. Number of petals/lobes: Divided into an entire lower lip and 4 toothed upper lip. Segments fused or free: Fused. Overall dimensions: 11 mm in length and 14 mm in diameter. Length of tube: No obvious tube. Length of spur: 9 mm. Color of spur: 1C. Lower lip: Shape: Rounded. Dimensions: Approximately 9 mm long and broad. Margin: Untoothed, not undulate. Color of inner surface: 76D near the margins, merging to 3D around raised palate. Palate is 15B. Color of outer surface: 84D near the margins merging to 4D around the back of the palate. Palate shape: appears as raised cuboid with rounded corners. Palate dimensions: 3 mm in width, 2.5 mm in depth and raised 1 mm. Palate surface texture: smooth, glossy. Upper lip; Shape: Deeply 4 lobed. Dimensions: Overall width 14 mm, overall length 13 mm. Outer lobes are larger than inner ones, approximately 7 mm long and 4 mm wide. Margin: Untoothed, not undulate. Color of inner surface: 76B with a small patch of 4B at the base. Color of outer surface: 76C.

*Reproductive organs.*—Number of stamens: 4. Filament dimensions: Less than 0.5 mm in width; upper stamens 2 mm in length, lower stamens less than 1 mm. Filament color: White. Anther dimensions: Less than 1 mm in length and less than 0.5 mm in width. Anther shape: Ellipsoid. Anther color: 160B. Pollen quantity: Moderate. Pollen color: 6D. Number of pistils: 1. Stigma shape: Unlobed. Stigma dimensions: Length and width both less than 0.5 mm. Stigma color: Pale green — too small to color match. Style dimensions: Length and width both less than 0.5 mm. Style color: Pale green — too small to color match. Ovary shape: Ovoid. Ovary position: Superior. Ovary dimensions: Length and width both less than 1 mm. Ovary color: N144D.

*Seed.*—None observed; plant is sterile.

It is claimed:

1. A new and distinct cultivar of *Nemesia* plant named 'Pendrop' as described and illustrated herein.

* * * * *